US009598713B2

(12) United States Patent
Abe et al.

(10) Patent No.: US 9,598,713 B2
(45) Date of Patent: Mar. 21, 2017

(54) METHOD FOR CONSTRUCTING FUNCTIONAL NUCLEIC ACID MOLECULE, AND NUCLEIC ACID COMBINATION TO BE USED IN SAID METHOD

(71) Applicant: JAPAN SCIENCE AND TECHNOLOGY AGENCY, Saitama (JP)

(72) Inventors: Hiroshi Abe, Saitama (JP); Yoshihiro Ito, Saitama (JP); Hideto Maruyama, Saitama (JP)

(73) Assignee: Japanese Science and Technology Agency, Saitama (JP)

( * ) Notice: Subject to any disclaimer, the term of this patent is extended or adjusted under 35 U.S.C. 154(b) by 190 days.

(21) Appl. No.: 14/381,681

(22) PCT Filed: Mar. 1, 2013

(86) PCT No.: PCT/JP2013/055732
§ 371 (c)(1),
(2) Date: Aug. 28, 2014

(87) PCT Pub. No.: WO2013/129663
PCT Pub. Date: Sep. 6, 2013

(65) Prior Publication Data
US 2015/0118713 A1  Apr. 30, 2015

(30) Foreign Application Priority Data
Mar. 2, 2012 (JP) .................. 2012-047367

(51) Int. Cl.
C12P 19/34 (2006.01)
C12N 15/10 (2006.01)
C12N 15/113 (2010.01)
C12N 15/11 (2006.01)

(52) U.S. Cl.
CPC .......... *C12P 19/34* (2013.01); *C12N 15/1068* (2013.01); *C12N 15/111* (2013.01); *C12N 15/113* (2013.01); *C12N 2310/14* (2013.01); *C12N 2310/315* (2013.01); *C12N 2330/30* (2013.01)

(58) Field of Classification Search
None
See application file for complete search history.

(56) References Cited

U.S. PATENT DOCUMENTS

| 6,184,037 | B1 | 2/2001 | Rolland et al. |
| 6,696,038 | B1 | 2/2004 | Mahato et al. |
| 2001/0031497 | A1 | 10/2001 | Rolland et al. |
| 2003/0073619 | A1 | 4/2003 | Mahato et al. |
| 2004/0142474 | A1 | 7/2004 | Mahato et al. |

FOREIGN PATENT DOCUMENTS

| AU | 199874010 B2 | 6/1998 |
| JP | 2000-510847 A | 8/2000 |
| JP | 2001514485 A | 9/2001 |
| JP | 2007-521247 A | 8/2007 |
| JP | 2008-259453 A | 10/2008 |

OTHER PUBLICATIONS

Maruyama, Hideto et al., "An intracellular buildup reaction of active siRNA species from short RNA fragments", Chemical Communications, vol. 50, No. 11, pp. 1284-1287, Feb. 9, 2014.
Shim, Min Suk et al., "Efficient and targeted delivery of siRNA in vivo", The FEBS Journal, vol. 277, No. 23, pp. 4814-4827, Dec. 2010.
Shegokar R et al., "SiRNA Delivery: challenges and role of carrier systems", Pharmazie, vol. 66, No. 5, pp. 313-318, Jun. 2011.
Higuchi, Yuriko et al., "Strategies for In Vivo Delivery of siRNAs", BioDrugs, vol. 24, Issue 3, pp. 195-205, Jun. 2010.
European Patent Office, "Extended European Search Report," issued in European Patent Application No. 13 755 064.6, which is a European Counterpart of U.S. Appl. No. 14/381,681 with an issuance date of Oct. 30, 2015, 5 pages.
Kondo Y et al., entitled "Multiple chemical ligation under thermal cycle," Nucleic Acids Symp. Ser., 2007, No. 51, pp. 353-354.
Abe H et al., entitled "Rapid DNA chemical ligation for amplification of RNA and DNA signal," Bioconjug. Chem., 2008, vol. 19, pp. 327-333.
Uda M et al., entitled "Synthesis of dumbbell-shaped nanocircular RNAs for improvement of permeability and stability," CSJ: The Chemical Society of Japan Dai 89 Shunki Nenkai Koen Yokoshu II, 2009, p. 1521, 3 PA-112.
Uda M et al., entitled "Development of modified dumbbell-shaped RNA interference," CSJ: The Chemical Society of Japan Dai 90 Shunki Nenkai Koen Yokoshu III, 2010, p. 785, 3 D4-55.
Taft R J et al., entitled "Non-coding RNAs: regulators of disease," Journal of Pathology, J Pathol 2010: 220: 126-139.
Fire A et al., entitled "Potent and specific genetic interference by double-stranded RNA in *Caenorhabditis elegans*," Nature, vol. 391, Feb. 1998, pp. 806-811.
Elbashir S M et al., entitled "Functional anatomy of siRNAs for mediating efficient RNAi in *Drosophila melanogaster* embryo lysate," The EMBO Journal, vol. 20, No. 23, pp. 6877-6888, 2001.
Burnett J C et al, entitled "Current Progress of siRNA/shRNA Therapeutics in Clinical Trials," Biotechnol J. Sep. 2011; 6(9): 1130-1146.
PCT International Search Report dated May 13, 2013 in connection with PCT International Application No. PCT/JP2013/055732, 4 pages.

*Primary Examiner* — Tracy Vivlemore
(74) *Attorney, Agent, or Firm* — Amster, Rothstein & Ebenstein LLP

(57) ABSTRACT

A method for constructing a functional nucleic acid molecule comprising 1 or 2 nucleic acid strands, wherein 2 or more fragments having at corresponding ends a functional group pair that can mutually couple through a chemical reaction are introduced into a cell, and a functional nucleic acid molecule comprising 1 or 2 nucleic acid strands is formed by ligating mutually the fragments through a reaction between the functional groups in the cell.

16 Claims, 6 Drawing Sheets

SEQUENCE LISTING

<160> NUMBER OF SEQ ID NOS: 6

<210> SEQ ID NO 1
<211> LENGTH: 25
<212> TYPE: RNA
<213> ORGANISM: Firefly

<400> SEQUENCE: 1
ccucauagaa cugccugcgu gagau                                          25

<210> SEQ ID NO 2
<211> LENGTH: 25
<212> TYPE: RNA
<213> ORGANISM: Firefly

<400> SEQUENCE: 2
aucucacgca ggcaguucua ugagg                                          25

<210> SEQ ID NO 3
<211> LENGTH: 19
<212> TYPE: DNA
<213> ORGANISM: Artificial Sequence
<220> FEATURE:
<223> OTHER INFORMATION: 3'-PS (phosphorothioate) RNA
<220> FEATURE:
<221> NAME/KEY: misc_feature
<223> OTHER INFORMATION: 1-18:RNA, 19:DNA

<400> SEQUENCE: 3
ccucauagaa cugccugcg                                                 19

<210> SEQ ID NO 4
<211> LENGTH: 18
<212> TYPE: DNA
<213> ORGANISM: Artificial Sequence

```
<220> FEATURE:
<223> OTHER INFORMATION: 3'-PS (phosphorothioate) RNA
<220> FEATURE:
<221> NAME/KEY: misc_feature
<223> OTHER INFORMATION: 1-17:RNA, 18:DNA

<400> SEQUENCE: 4
aucucacgca ggcaguuc                                               18

<210> SEQ ID NO 5
<211> LENGTH: 25
<212> TYPE: DNA
<213> ORGANISM: Artificial Sequence
<220> FEATURE:
<223> OTHER INFORMATION: ligated siRNA
<220> FEATURE:
<221> NAME/KEY: misc_feature
<223> OTHER INFORMATION: 1-18:RNA, 19-20:DNA, 21-25:RNA

<400> SEQUENCE: 5
ccucauagaa cugccugcgt gagau                                       25

<210> SEQ ID NO 6
<211> LENGTH: 25
<212> TYPE: DNA
<213> ORGANISM: Artificial Sequence
<220> FEATURE:
<223> OTHER INFORMATION: ligated siRNA
<220> FEATURE:
<221> NAME/KEY: misc_feature
<223> OTHER INFORMATION: 1-17:RNA, 18-19:DNA, 20-25:RNA

<400> SEQUENCE: 6
aucucacgca ggcaguucta ugagg                                       25
```

METHOD FOR CONSTRUCTING FUNCTIONAL NUCLEIC ACID MOLECULE, AND NUCLEIC ACID COMBINATION TO BE USED IN SAID METHOD

CROSS-REFERENCE TO RELATED APPLICATIONS

This application is a U.S. national stage entry under 35 U.S.C. §371 of PCT International Patent Application No. PCT/JP2013/055732, filed Mar. 1, 2013, which claims the benefit of Japanese Patent Application No. 2012-047367, filed Mar. 2, 2012, the contents of which are incorporated herein by reference into the subject application.

TECHNICAL FIELD

The present invention relates to a novel method for constructing a functional nucleic acid molecule in a cell, and to a nucleic acid combination to be used in said method.

BACKGROUND ART

Among nucleic acid molecules, molecules which do not code for a protein but perform a function important for various life phenomena have been known. Examples of such nucleic acid molecules include a functional non-coding RNA molecule (Non Patent Literature 1) and a small RNA molecule that induces RNA interference (Non Patent Literature 2).

For example, RNA interference has been energetically studied as an important technique for suppressing specifically an action of a target RNA in a cell (Non Patent Literature 3) for an application not only as a reagent but also as a drug (Non Patent Literature 4).

CITATION LIST

Non Patent Literature

Non Patent Literature 1: Ryan J Taft, Ken C Pang, Timothy R Mercer, Marcel Dinger, and John S Mattick; J Pathol., 2010, 220, 126-139.
Non Patent Literature 2: Fire A, Xu S, Montgomery M, Kostas S, Driver S, Mello C; Nature, 1998, 391, 806-11.
Non Patent Literature 3: Sayda M. Elbashir, Javier Martinez, Agnieszka Patkaniowska, Winfried Lendeckel, and Thomas Tuschl; EMBO J., 2001, 20, 6877-6888.
Non Patent Literature 4: John C. Burnett, John J. Rossi, and Katrin Tiemann; Biotechnol. J., 2011, 6, 1130-1146.

SUMMARY OF INVENTION

Technical Problem

Although an RNA inducing RNA interference is a small molecule, further improvement permeability of cell membrane and also required suppression of the development of toxicity caused by activation of the immune system are required for exploiting its effect maximally.

However, in response to such requirements, only an endeavor has been made until now to downsize further an RNA molecule by reducing the sequence to the minimum required for carrying out the function.

In view of such a situation, the present invention was made with an object to provide a method for introducing a functional nucleic acid molecule into a cell after making the molecule into a form to be easily incorporated into a cell, and then constructing the functional nucleic acid molecule in the cell.

Solution to Problem

To achieve the object, the present invention provides a method for constructing a functional nucleic acid molecule comprising 1 or 2 nucleic acid strands, comprising an introducing step for introducing 2 or more fragments having at corresponding ends a functional group pair that can mutually couple through a chemical reaction into a cell, and a producing step for producing a functional nucleic acid molecule comprising 1 or 2 nucleic acid strands by ligating mutually the fragments through a reaction between the functional groups in the cell.

The present invention also provides a nucleic acid combination for constructing a functional nucleic acid molecule to be used in the above method, comprising the nucleic acid strands constituting a functional nucleic acid molecule, wherein at least one of the nucleic acid strands is contained as 2 or more fragments having at corresponding ends a functional group pair that can mutually couple through a chemical reaction.

Advantageous Effects of Invention

A functional nucleic acid molecule can be constructed in a cell by introducing, in the cell, the functional nucleic acid molecule as a plurality of fragments which can be easily incorporated into a cell.

DESCRIPTION OF EMBODIMENTS

Figure 1:
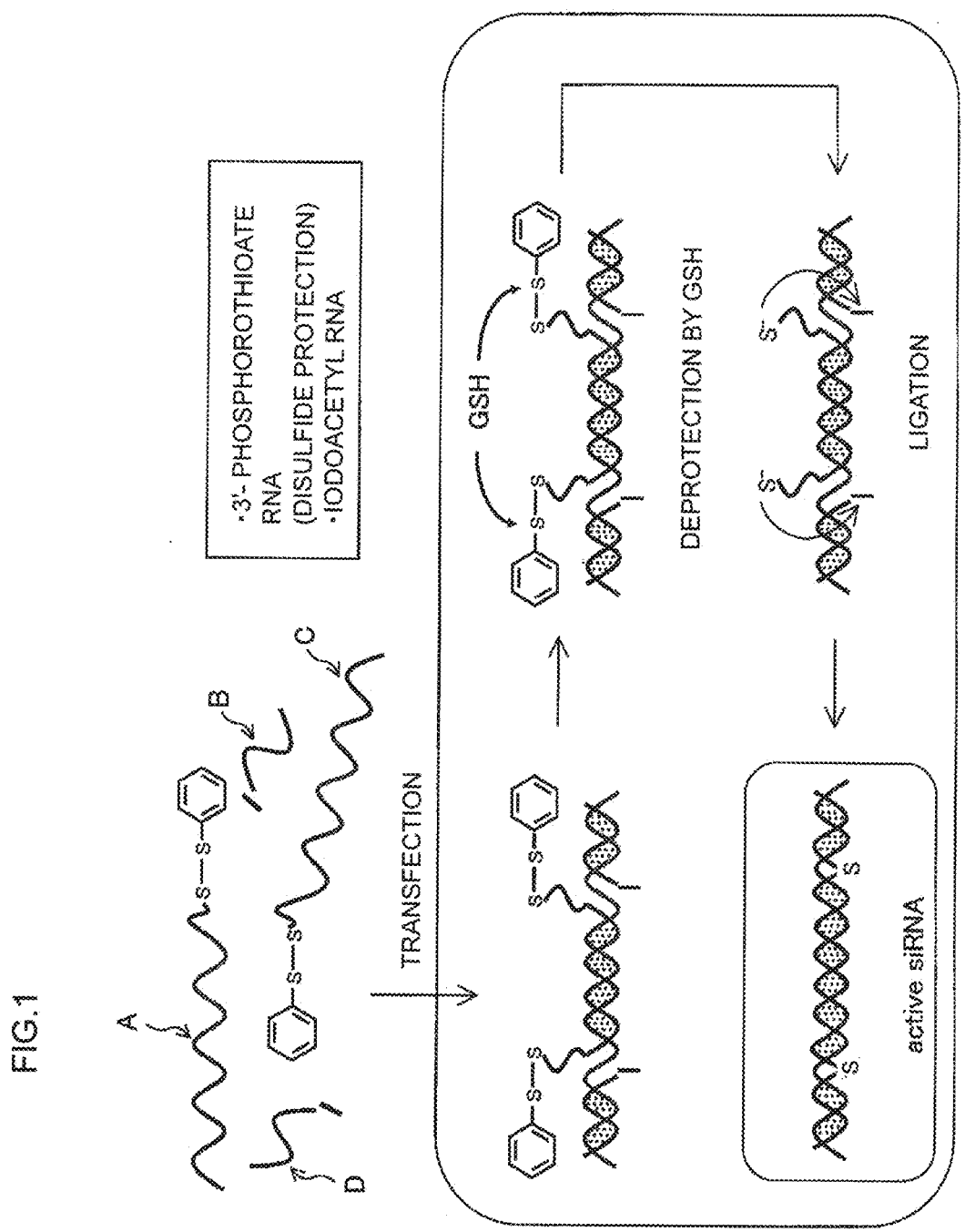
FIG. 1 is a schematic diagram of an embodiment of a method according to the present invention.

1. Method for Constructing Functional Nucleic Acid Molecule (Outline of Construction Method)
A method for constructing a functional nucleic acid molecule according to the present invention is a method for constructing a functional nucleic acid molecule comprising 1 or 2 nucleic acid strands and includes the following steps 1) and 2):
1) an introducing step for introducing 2 or more fragments having at corresponding ends a functional group pair that can mutually couple through a chemical reaction into a cell; and 2) a producing step for producing a functional nucleic acid molecule comprising 1 or 2 nucleic acid strands by ligating mutually the fragments through a reaction between the functional groups in the cell.

In other words, a method for constructing a functional nucleic acid molecule according to the present invention is a method for constructing a functional nucleic acid molecule comprising 1 or 2 nucleic acid strands and includes the following steps 1) and 2):

1) an introducing step for making at least one of the nucleic acid strands into 2 or more fragments having at corresponding ends a functional group pair that can mutually couple through a chemical reaction, and then introducing the 1 or 2 nucleic acid strands (namely, one of the strands has been made into 2 or more fragments) into a cell; and 2) a producing step for producing a functional nucleic acid molecule comprising 1 or 2 nucleic acid strands by ligating mutually the fragments through a reaction between the functional groups in the cell.

According to the construction method, at least a part of nucleic acid strands constituting a functional nucleic acid molecule is introduced in a cell as a plurality of fragments, and a functional nucleic acid molecule is constructed in a cell. Consequently, incorporation of a functional nucleic acid molecule into a cell is improved. Furthermore, since at least a part of nucleic acid strands is used as shorter fragments, immunotoxicity due to a functional nucleic acid molecule can be suppressed.

(Functional Nucleic Acid Molecule)

A functional nucleic acid molecule means herein a nucleic acid molecule which is constituted of a plurality of nucleic acids linked as a chain (namely, oligo- or polynucleotide), does not code for a protein, but exhibits a certain function with respect to a life phenomenon, such as development and differentiation. Therefore, a primer and a probe, which only hybridize with a specific target but do not exert a particular function with respect to a life phenomenon, are excluded from the category of the functional nucleic acid molecule according to the present invention.

A functional nucleic acid molecule is a DNA molecule, an RNA molecule, or a DNA-RNA hybrid molecule. A functional nucleic acid molecule may be constituted of one nucleic acid strand or two nucleic acid strands. Furthermore, a functional nucleic acid molecule may contain as a part a non-natural nucleic acid. In this regard, the term "nucleic acid strand" means herein a full-length nucleic acid strand in a state constituting a functional nucleic acid molecule, and is discriminated from a term "fragment" (described later) which corresponds to shorter pieces cut from the "nucleic acid strand".

Examples of the DNA molecule include a DNA aptamer; a CpG motif; and a DNAzyme. In this regard, a strand based on a DNA strand, to which an RNA and/or a non-natural nucleic acid or the like is inserted partly, is classified herein as a DNA molecule.

Examples of the RNA molecule include an RNA aptamer; an RNA molecule exhibiting an RNA interference action (nucleic acid molecule for RNAi), such as an shRNA, an siRNA, and a microRNA; an antisense RNA molecule; and an RNA ribozyme. In this regard, a strand based on an RNA strand, to which a DNA and/or a non-natural nucleic acid or the like is inserted partly, is classified herein as an RNA molecule.

Examples of the DNA-RNA hybrid molecule include a DNA-RNA hybrid aptamer.

A functional nucleic acid molecule preferably forms a hybridization region where hybridization occurs within the nucleic acid strand or between different nucleic acid strands for the sake of exerting the function. For a reason behind the above, see also the description in the section of (Preferable Design of Fragments of Nucleic Acid Strand) below.

A functional nucleic acid molecule is more preferably a nucleic acid molecule for RNAi having a hybridization region where hybridization occurs within the nucleic acid strand or between different nucleic acid strands, and further preferably a nucleic acid molecule for RNAi comprising 2 nucleic acid strands. The nucleic acid strand length (mer) of a nucleic acid molecule for RNAi comprising 2 nucleic acid strands is, for example, from 15 to 40 mer, preferably from 15 to 35 mer, and more preferably from 20 to 35 mer.

(Fragments of Nucleic Acid Strand)

"Fragments" of a nucleic acid strand constituting a functional nucleic acid molecule correspond to 2 or more nucleic acid molecules divided from the "nucleic acid strand". When all the "fragments" originated from a nucleic acid strand are ligated in a proper order, a nucleic acid molecule having the same nucleotide sequence as the nucleic acid strand is constructed. However, by the term "fragment", it is not meant that the fragment is prepared by division of a nucleic acid strand once constructed.

In the case of construction of a nucleic acid strand constituting a functional nucleic acid molecule by ligating fragments, a 3' end and a 5' end belonging to different fragments are coupled mutually. In this case, a combination of a 3' end and a 5' end to be coupled mutually is referred to as "corresponding ends". In other words, "corresponding ends" form adjacent ends, when fragments are aligned to constitute a nucleic acid strand, on which designs of the fragments are based.

Although there is no particular limitation on the length of a "fragment" originated from a nucleic acid strand, it is occasionally preferable that the difference in length (mer) between different fragments is not too large. From this viewpoint, with respect to the longest "fragment" originated from a nucleic acid strand, the lengths of all other fragments are preferably not less than [25%×length (mer) of the longest fragment], and more preferably not less than [30%×length (mer) of the longest fragment].

The "corresponding ends" are bonded with a functional group pair (a combination of functional groups), which mutually couple through a chemical reaction, and a nucleic acid strand is made by ligating mutually the fragments by a reaction between the functional groups.

Although there is no particular limitation on the functional group pair, for example, a combination of an electrophilic group and a nucleophilic group is preferable. In other words, an electrophilic group is bonded to one of the "corresponding ends", and a nucleophilic group is bonded to the other of the "corresponding ends", and the two different fragments are mutually ligated through a chemical reaction. In this regard, an electrophilic group and a nucleophilic group may be bonded to either of a 3' end and a 5' end. Namely, an electrophilic group may be bonded to the 3' end and a nucleophilic group to the 5' end, or alternatively, an electrophilic group may be bonded to the 5' end and a nucleophilic group to the 3' end.

Although there is no particular limitation on the electrophilic group, examples thereof include a halogenated alkyl group, such as an iodoacetyl group (reference literature: Bioconjugate, Chem., 2008, 19, 327), and a bromoacetyl group (reference literature: Nucleic Acids Res., 22, 5076); a halogen group, such as an iodo group (reference literature: Tetrahedron Lett., 1995, 38, 55959) and a bromo group; and a formyl group. In an embodiment, it may be preferable that an electrophilic group is an iodoacetyl group, a bromoacetyl group, or an iodo group.

Although there is no particular limitation on the nucleophilic group, examples thereof include a phosphorothioate group; a thiol group; a hydroxy group; an amino group; an alkylthio group such as a thiomethyl group; and an alkoxy group such as a methoxy group. In an embodiment, it is occasionally preferable that the nucleophilic group is a phosphorothioate group.

Although there is also no particular limitation on a combination of the electrophilic group and the nucleophilic group constituting a functional group pair, a combination of a halogenated alkyl group or a halogen group, and a phosphorothioate group, or a combination of a halogenated alkyl group or a halogen group, and a thiol group is occasionally preferable. In an embodiment, a combination of the electrophilic group and the nucleophilic group constituting a functional group pair is occasionally more preferably a combination of an iodoacetyl group, a bromoacetyl group, or an iodo group, and a phosphorothioate group.

An example of a preferable combination of the electrophilic group and the nucleophilic group attached to corresponding ends, and a form of mutual coupling of the groups through a chemical reaction are shown below. In the chemical formulas with respect to a sugar, only a backbone moiety is shown, and the sugar may be either of a ribose and a deoxyribose. Furthermore, B in the chemical formulas stands for various bases constituting a nucleic acid. For example, although cases where a functional nucleic acid molecule is an RNA molecule are shown in the following examples, a similar constitution is also possible for a DNA molecule.

[Formula 1]

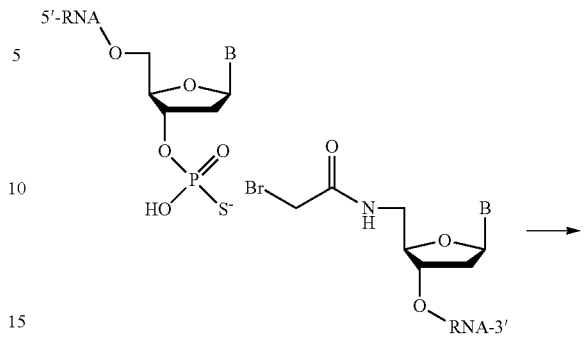

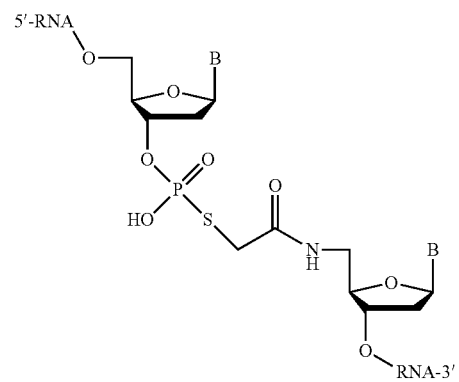

3'-phosphorothioate group + 5'-bromoacetyl group

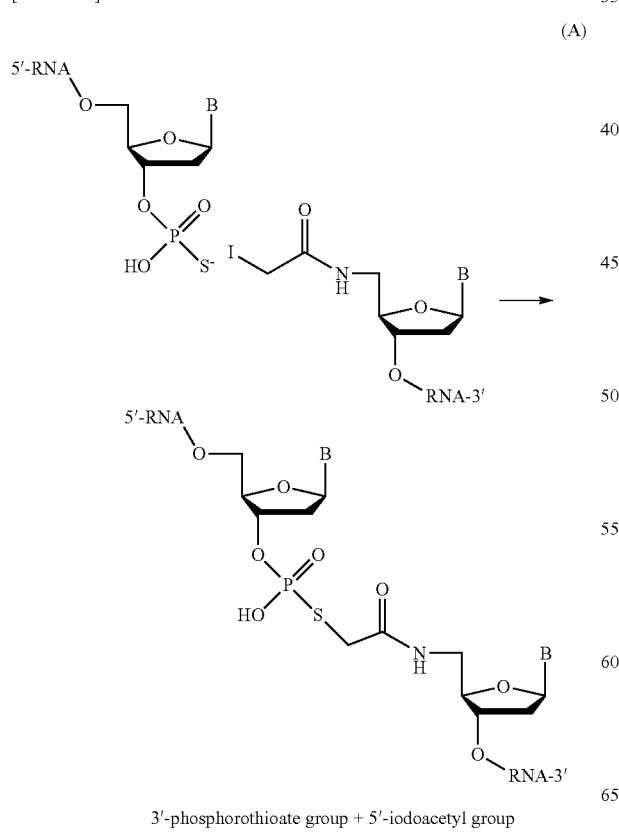

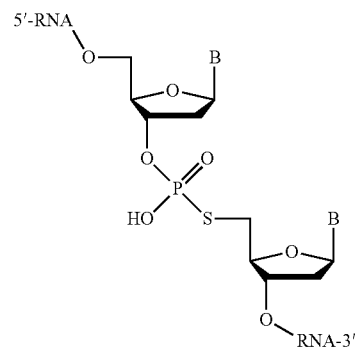

3'-phosphorothioate group + 5'-iodoacetyl group

3'-phosphorothioate group + 5'-iodo group

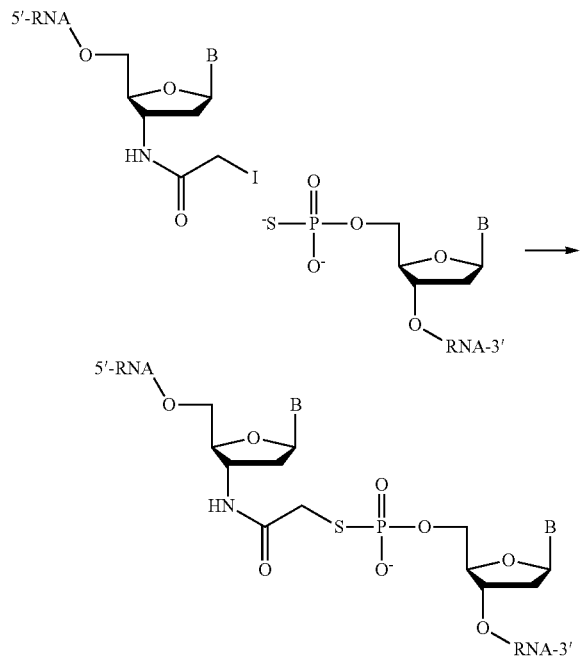

3'-iodoacetyl group + 5'-phosphorothioate group

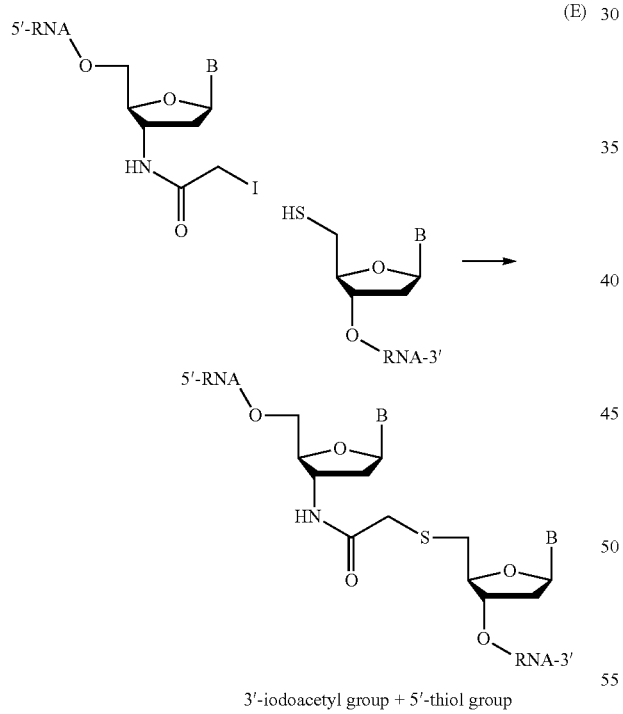

3'-iodoacetyl group + 5'-thiol group

Especially when a plurality of fragments to be ligated mutually should be present concurrently in a system, it is preferable that the nucleophilic group is protected by a protecting group which can be deprotected at a desired timing, so that the percentage of fragments mutually ligated outside a cell can be reduced (substantially to zero). In other words, a functional group pair is preferably, in an embodiment, a combination of an electrophilic group and a nucleophilic group protected by a protecting group.

A type of a protecting group for protecting a nucleophilic group may be adopted appropriately according to the type of a nucleophilic group. Examples of a preferable protecting group include one that can be eliminated from a nucleophilic group by an action of an endogenous substance in a cell. An "endogenous substance in a cell" forms a counterpart to a "substance imported from outside of a cell" described later, and means a substance that the cell retains intrinsically. Examples of an endogenous substance in a cell include an enzyme and a peptide. An enzyme, a peptide, etc. expressed in a cell transgenically are within a category of an endogenous substance in a cell, because the substances per se are not "imported from outside of a cell".

Examples of the protecting group usable for protecting a phosphorothioate group among protecting groups, which can be eliminated from a nucleophilic group by an action of an endogenous substance in a cell, include those capable of protecting a phosphorothioate group by means of disulfide protection, such as a phenyl thio group (a) and another arylthio group; a nitrobenzyl group (b), an ester (c, d), thiocarbonyl (e), and an amide (f); of which structures are shown below, as well as derivatives thereof. With respect to the nitrobenzyl group, any of an o-nitrobenzyl group, an m-nitrobenzyl group, and a p-nitrobenzyl group may be used, however, from a viewpoint of reactivity an m-nitrobenzyl group, and a p-nitrobenzyl group are preferable.

[Formula 2]

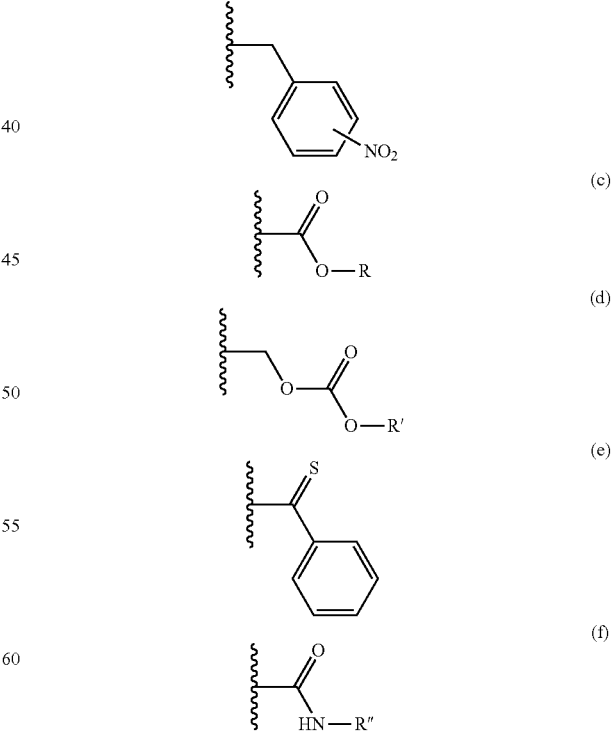

There is no particular limitation on R, R' and R" in (c), (d), and (f) insofar as the spirit of the present invention is not impaired, and they preferably represent, for example, a substituted or unsubstituted alkyl group or aryl group. The alkyl group or the aryl group may contain, for example, 1 to 15 carbon atoms, and preferably 1 to 10 carbon atoms. Examples of the alkyl group include linear alkyl groups, such as a methyl group, an ethyl group, an n-propyl group, an isopropyl group, an n-butyl group, an isobutyl group, a sec-butyl group, a tert-butyl group, an n-pentyl group, an isopentyl group, a hexyl group, a 2-ethylhexyl group, a heptyl group, an octyl group, a nonyl group, and a decyl group; and cyclic alkyl groups, such as a cyclopropyl group, a cyclobutyl group, a cyclopentyl group, a cyclohexyl group, a cycloheptyl group, a cyclooctyl group, a cyclononyl group, a cyclodecyl group, and an adamantyl group. Examples of the aryl group include a phenyl group, a tolyl group, and a naphthyl group.

Examples of a substituent possessed by the alkyl group or the aryl group include a halogen atom (fluorine, chlorine, bromine, and iodine), a hydroxy group, a C1 to C10 (preferably C1 to C4) alkyl group (a linear or cyclic alkyl group), a C1 to C4 alkoxy group, a C1 to C5 acyloxy group, a carboxyl group, a C2 to C5 alkoxycarbonyl group, a C6 to C10 aryl group, a cyano group, and a nitro group. Meanwhile, when a plurality of the linear alkyl groups are present as substituents on an aryl group, the linear alkyl groups may together form a ring, and 1 to several (preferably 1 to 3) carbon atoms in the ring may be substituted with oxygen atom(s). For example, alkyl substituents positioned at adjacent carbon atoms in an aryl group form together a ring, and 2 carbon atoms are replaced by oxygen atoms to form a 1,3-dioxolane-like cyclic structure.

Examples of an alkyl group having a cyclic alkyl group as a substituent include a cyclopentylmethyl group, a cyclopentylethyl group, a cyclopentylpropyl group, a cyclohexylmethyl group, a cyclohexylethyl group, and a cyclohexylpropyl group. Examples of an alkyl group having an aryl group as a substituent include a benzyl group, a phenylethyl group, a phenylpropyl group, a naphthalenylmethyl group, a naphthalenylethyl group, and a naphthalenylpropyl group.

Meanwhile, an aryl group may form a heterocyclic ring by replacing a part of the skeleton by a nitrogen atom, an oxygen atom, a sulfur atom, or the like. Furthermore, a plurality of hydrogen atoms on a benzene ring in (a), (b), and (e) may be substituted independently with a substituent. Therefore, examples of a derivative of (a), (b), and (e) include those in which some hydrogen atoms (for example, 1 to 3) on the benzene ring in (a), (b), or (e) are replaced by any of the substituents listed above.

A phenylthio group is reduced by a thiol source in the body such as GSH (glutathione) existing in a cell and eliminated. A nitrobenzyl group is reduced by a nitroreductase existing in a cell and eliminated (reference literature: Bioorg. Med. Chem., 11, 2453). An ester and a thiocarbonyl are eliminated by an esterase existing in a cell. An amide is eliminated by a peptidase existing in a cell.

If a phosphorothioate group is protected by a protecting group such as (a) to (f) described above, the phosphorothioate group is substantially not deprotected outside a cell. Therefore, even if fragments of a nucleic acid strand are simply mixed outside a cell, a coupling reaction does not take place. Consequently, the probability of introduction of the short-remaining fragments into a cell by a single operation increases. Furthermore, since a deprotection reaction occurs spontaneously by an enzyme or a peptide existing in the cell, both an introducing step and a producing step can be carried out by a single operation.

Examples of the protecting group for protecting a phosphorothioate group include, in addition to the above, those to be eliminated from a nucleophilic group by light irradiation. Examples of such a protecting group include the following (g) to (j) and derivatives thereof (reference literature: Molecular Pharmaceutics, 2009, 6, 669).

[Formula 3]

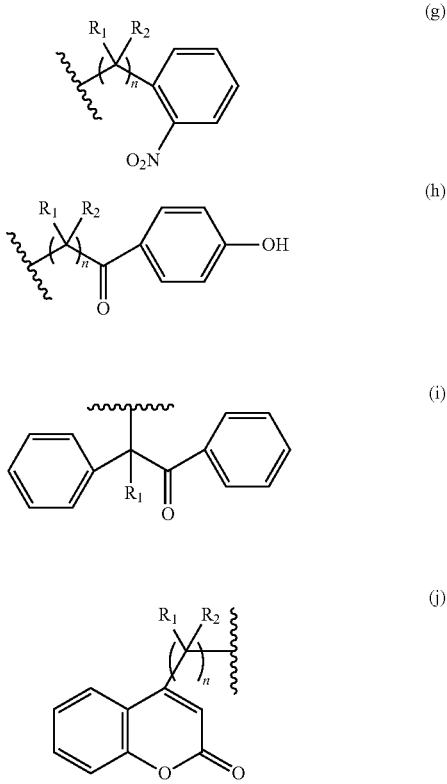

Although there is no particular limitation on $R_1$, $R_2$ and n in (g) to (j), insofar as a spirit of the present invention is not impaired, for example, $R_1$ and $R_2$ independently represent a hydrogen atom or a C1 to C4 alkyl group, n represents an integer from 1 to 3, but in (g), preferably 1 or 2, and in (h) and (j), preferably 1. Meanwhile, when n is 2 or 3, n number of $R_1$ may be different from each other, and n number of $R_2$ may be different from each other. Furthermore, a plurality of hydrogen atoms on a benzene ring in (g) to (j) may be independently replaced by a substituent. Therefore, examples of a derivative of (g) to (j) include those in which some hydrogen atoms (for example, 1 to 3) on the benzene ring in (g) to (j) are replaced by any of the substituents listed above.

If a phosphorothioate group is protected by a protecting group such as (g) to (j) described above, the phosphorothioate group is substantially not deprotected outside a cell under a condition that the protecting group is not irradiated with light having a wavelength required for eliminating the same. Therefore, even if fragments of a nucleic acid strand are simply mixed outside a cell, a coupling reaction does not take place. Consequently, the probability of introduction of the short-remaining fragments into a cell by a single operation increases. Furthermore, by regulating the timing of light irradiation, a deprotection reaction can be implemented at a desired timing.

Specific examples of (g) above and a derivative thereof include the following groups.

[Formula 4]

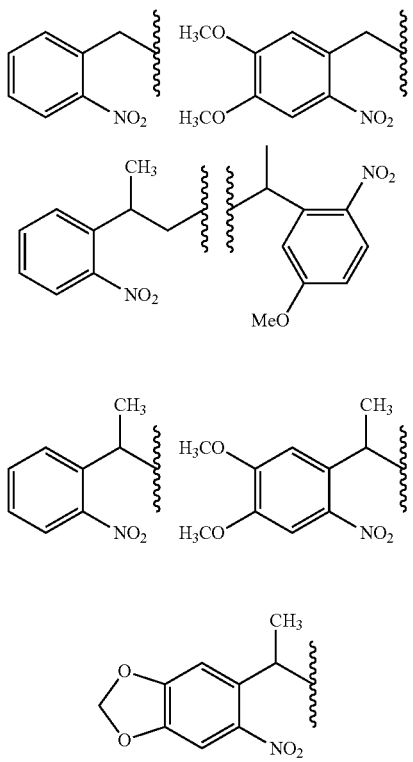

Specific examples of (h) above include the following groups.

[Formula 5]

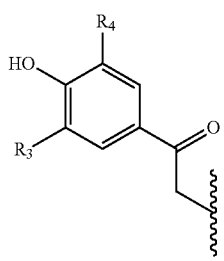

Specific examples of (i) above include the following groups.

[Formula 6]

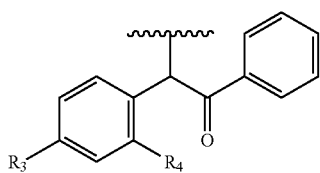

Specific examples of (j) above include the following groups.

[Formula 7]

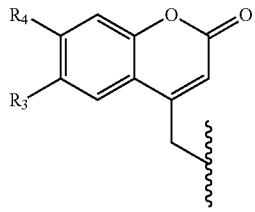

$R_3$ and $R_4$ in the protecting groups independently represent any of the substituents, which may be substituted on an aryl group as listed above.

Protecting groups for protecting a phosphorothioate group include, in addition to the above, a protecting group which is eliminated by a substance imported from outside of a cell. Examples of such a protecting group include an azidobenzyl group (k) and a derivative thereof. As for an azidobenzyl group, any of an o-azidobenzyl group, an m-azidobenzyl group, and a p-azidobenzyl group may be used, and a p-azidobenzyl group is preferable from a viewpoint of reactivity. Furthermore, a plurality of hydrogen atoms on a benzene ring in (k) may be independently replaced by a substituent. Therefore, examples of a derivative of (k) include those in which some hydrogen atoms (for example, 1 to 3) on the benzene ring in (k) are replaced by any of the substituents listed above.

[Formula 8]

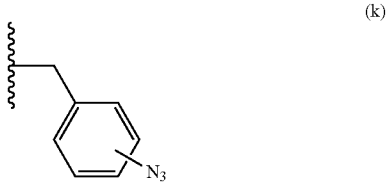

(k)

An azidobenzyl group is eliminated by importing a phosphine into a cell (reference literature: Bioconjugate, Chem., 2008, 19, 714). The phosphine is preferably a water-soluble phosphine from a viewpoint of membrane permeability.

When a phosphorothioate group is protected by a protecting group such as (k) above, the phosphorothioate group is substantially not deprotected outside a cell. Therefore, even if fragments of a nucleic acid strand are simply mixed outside a cell, a coupling reaction does not take place. Consequently, the probability of introduction of the short-remaining fragments into a cell by a single operation increases. Furthermore, by regulating the timing of import of an active substance for deprotection (phosphine, etc.), a deprotection reaction can be implemented at a desired timing.

Examples of a functional group pair, which react each other only under a predetermined condition to couple, include, in addition to those using the deprotection reaction as above, a combination of a phosphorodiester group and an iodo group (reference literature: J. Mol. Evol., 2003, 56, 607). When the combination is used, a coupling reaction can be initiated by introducing cyanogen bromide (BrCN) into a cell.

[Formula 9]

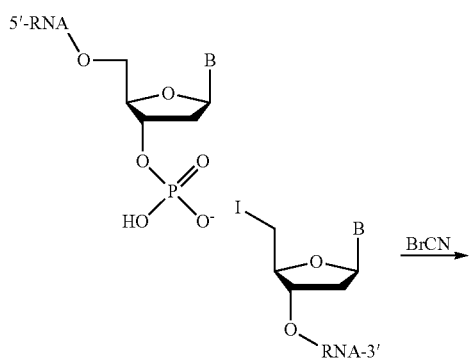

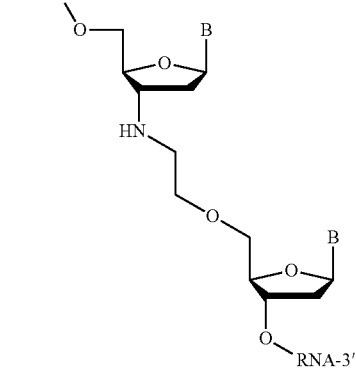

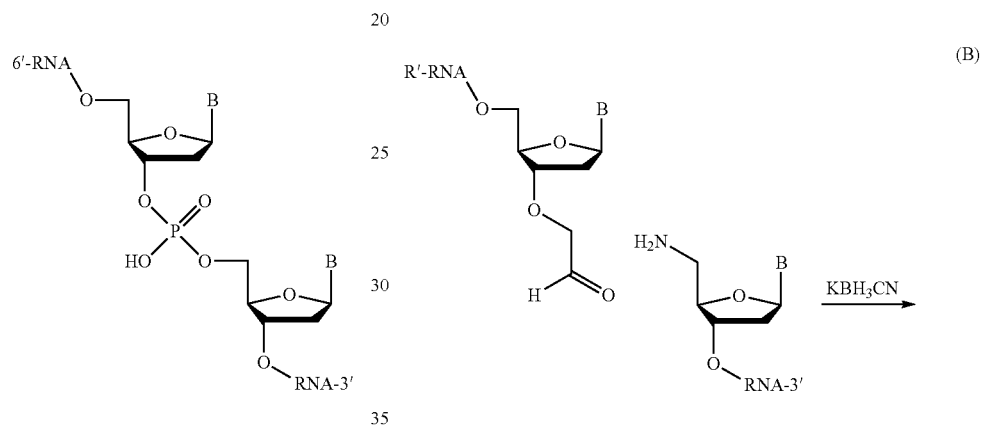

Examples of the functional group pair further include a combination of an amino group and an aldehyde group (reference literature: J. Am. Chem. Soc., 2005, 127, 10144; and J. Am. Chem. Soc., 1997, 1119, 12420). When the combination is used, a coupling reaction can be initiated by introducing sodium cyanoborohydride (NaCNBH$_3$) or potassium cyanoborohydride (KBH$_3$CN) into a cell.

[Formula 10]

(A)

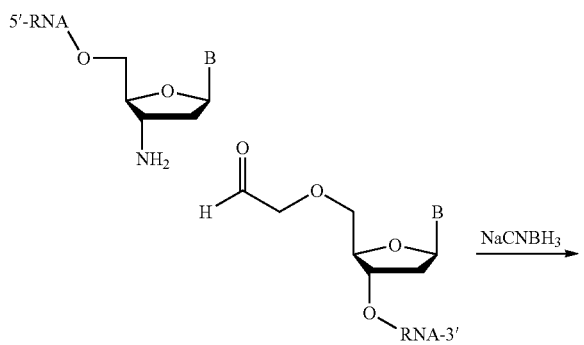

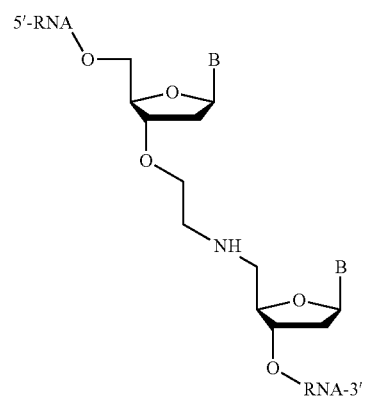

Examples of the functional group pair further include a combination of an azido group and an alkynyl group (reference literature: PNAS, 2010, vol. 107, 15329-15334, and ChemBioChem, 2011, 12, 125-131). When the combination is used, a coupling reaction can be initiated by introducing copper into a cell.

[Formula 11]

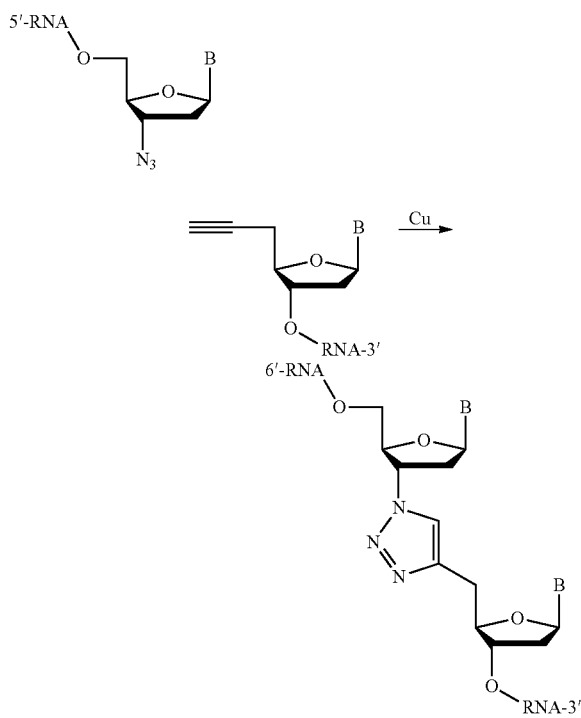

In the chemical formulas with respect to a sugar, only a backbone moiety is shown, and the sugar may be either of a ribose and a deoxyribose. Furthermore, B in the chemical formulas stands for various bases constituting a nucleic acid. For example, although in the above example cases where a functional nucleic acid molecule is an RNA molecule are shown, a similar constitution is also possible with a DNA molecule.

When a functional nucleic acid molecule is composed of 2 nucleic acid strands, it is required that at least one of the strands is in a form of 2 or more fragments, but it is preferable that both the strands are in a form of 2 or more fragments.

(Method for Preparing Fragments of Nucleic Acid Strand)

There is no particular limitation on a method for preparing "fragments" of a nucleic acid strand having the functional groups at their ends. A part of an oligonucleotide of the fragment can be synthesized, for example, by an in vitro transcription synthesis method, a method using a plasmid or a virus vector, or a method using a PCR cassette. From viewpoints of high purity, possibility of synthesis in a large amount, high safety in use in vivo, and possibility of chemical modification, a chemical synthesis method is preferable. Examples of a chemical synthesis method include a phosphoramidite method, and an H-phosphonate method, and a commercially-supplied nucleic acid synthesizer can be used.

As for a method for attaching a predetermined functional group and a protecting group to the 3' end and the 5' end (corresponding ends) of an oligonucleotide, a publicly known method according to the type of a functional group may be used. Meanwhile, from a viewpoint of relative easiness in introduction of a functional group, etc., deoxyribose nucleic acids are preferable as nucleic acids constituting "corresponding ends" irrespective of the type of a "nucleic acid strand", and those selected from dA, dG, dC, and dT are more preferable.

The thus prepared fragment is preferably purified prior to the introducing step for some end uses from a viewpoint of safety for use in vivo. Furthermore, in order to increase the cell membrane permeability of a fragment, a cell membrane permeable molecule may be bonded to the fragment. Examples of such a molecule include a membrane permeable peptide, such as a TAT peptide, oligo-arginine, penetratin, and TP-10; cholesterol; and vitamin A.

(Preferable Design of Fragments of Nucleic Acid Strand)

In a case where the functional nucleic acid molecule forms a hybridization region by hybridization within a nucleic acid strand or hybridization between different nucleic acid strands for the sake of exerting the function, fragments of the nucleic acid strand are preferably designed such that ligation of the fragments occurs within the hybridization region. The above will be described more specifically below referring to FIG. 1.

FIG. 1 shows an example of a preferable design of an siRNA as a functional nucleic acid molecule (see also Example). In the current example, an siRNA is so constituted that a first RNA strand and a second RNA strand hybridize together.

A first RNA strand is present as a first fragment (A in FIG. 1) having a phosphorothioate group (one member of a functional group pair) at the 3' end and a second fragment (B in FIG. 1) having an iodoacetyl group (the other member of the functional group pair) at the 5' end. Meanwhile, a second RNA strand is present as a third fragment (C in FIG. 1) having a phosphorothioate group (one member of a functional group pair) at the 3' end and a fourth fragment (D in FIG. 1) having an iodoacetyl group (the other member of the functional group pair) at the 5' end. Both the phosphorothioate groups are protected by a phenylthio group (protecting group).

The first RNA strand and the second RNA strand are designed such that the strands are fragmentized into 2 pieces respectively at different positions. In other words, both the first fragment and the second fragment constituting a first RNA strand hybridize with the third fragment such that the two adjoin each other. Similarly, both the third fragment and the fourth fragment constituting a second RNA strand hybridize with the first fragment such that the two adjoin each other. According to the above, the corresponding ends having a functional group are present in the vicinity with respect to both the first RNA strand and the second RNA strand, coupling reactions between the functional groups can be implemented efficiently in the producing step.

Although FIG. 1 shows a case where a coupling of fragments constituting a first RNA strand and a coupling of fragments constituting a second RNA strand occur at different places (positions different from each other) in a hybridization region, a case where only one of the first RNA strand and the second RNA strand in FIG. 1 is fragmentized is also a preferable example of fragmentation, from a viewpoint of putting efficiently the corresponding ends close to each other.

Although an siRNA is shown as an example of a functional nucleic acid molecule in FIG. 1, the design of fragments shown in FIG. 1 can be applied widely to a functional nucleic acid molecule that forms a hybridization region by hybridization within a nucleic acid strand or hybridization between different nucleic acid strands.

(Introducing Step)

An introducing step is a step in which at least one of the "nucleic acid strands" to compose a functional nucleic acid molecule is prepared in a form of 2 or more "fragments" having a "functional group pair" at "corresponding ends"

that will couple mutually through a chemical reaction, and then all the nucleic acid strands to compose the functional nucleic acid molecule are introduced into a cell. The definitions for "nucleic acid strand", "functional group pair", "corresponding ends", and "fragment" are the same as above.

More specifically, for example, a "nucleic acid combination" according to any one of the following 1) to 3) is introduced into a cell in the introducing step. In this regard, a "nucleic acid combination" means a combination of 2 or more nucleic acid molecules, which may be in a form of a mixed composition, or in a form isolated from each other (not mixed) by storage in separate preservation containers and the like.

1) In a case where a functional nucleic acid molecule is composed of a nucleic acid strand, "nucleic acid combination" refers to the 2 or more "fragments" for constructing the nucleic acid strand. It is preferable that all nucleic acid molecules are contained in nearly equal amounts (numbers).

2) In a case where a functional nucleic acid molecule is composed of 2 nucleic acid strands, "nucleic acid combination" refers to the 2 or more "fragments" for constructing one of the nucleic acid strands, and the other nucleic acid strand. It is preferable that all nucleic acid molecules are contained in nearly equal amounts (numbers).

3) In a case where a functional nucleic acid molecule is composed of 2 nucleic acid strands, "nucleic acid combination" refers to the 2 or more "fragments" for constructing one of the nucleic acid strands, and the 2 or more "fragments" for constructing the other nucleic acid strand. It is preferable that all nucleic acid molecules are contained in nearly equal amounts (numbers).

There is no particular limitation on a target cell to which a nucleic acid combination is to be introduced. A target cell may be either of a prokaryotic cell and a eukaryotic cell. Examples of a eukaryotic cell include cells originated from a fungus, a plant, and an animal. Examples of an animal cell include a nonmammalian cell such as an insect cell, and a mammalian cell. Examples of a mammalian cell include cells of a non-human animal, such as a rodent like a mouse, a rat, and a guinea pig, a rabbit, a dog, and a cat, and a human cell. The cell may be a cultured cell or a biological cell (a cell not isolated and in the body). Preferable examples of a cell include a cultured human cell, a human biological cell, a cultured cell of a non-human pathological model animal, and a biological cell of a non-human pathological model animal.

There is no particular limitation on an introduction method of a nucleic acid combination. Examples of an in vitro introduction method include an electroporation method, a microinjection method, a lipofection method, and a calcium phosphate method. Examples of an in vivo introduction method include a local administration, an intravenous administration, and a method using a gene gun. In the case of an application to a human body or a non-human animal body, a method not using a microorganism is preferable from a viewpoint of safety. Furthermore, it is preferable that a sample containing a nucleic acid combination is so prepared as to become compatible with an organism by dialysis or pH adjustment before in vivo introduction. Furthermore, in the case of an in vivo application, a pharmaceutical composition (e.g., liposome preparation) may be produced by combining, according to need, a pharmaceutically permissible carrier.

All nucleic acid molecules constituting a nucleic acid combination may be mixed and introduced as a nucleic acid composition into a cell by one-time operation, or each of the nucleic acid molecules may be introduced individually into a cell. Similarly, 2 or more fragments for constructing a nucleic acid strand may be introduced into a cell by one-time operation, or each of them may be introduced individually into a cell.

(Producing Step)

In a producing step, 2 or more "fragments" having the "functional group pair" at "corresponding ends" are ligated in a cell in which a nucleic acid combination has been introduced in the introducing step. In other words, a chemical reaction progresses between the functional group pair, so that the "corresponding ends" are coupled mutually (chemical ligation=nonenzymatical ligation) and a nucleic acid strand which has been in a form of "fragments" is constructed as a continuous nucleic acid strand. In addition, by causing, according to need, interaction such as hybridization within a nucleic acid strand or between different nucleic acid strands, a functional nucleic acid molecule is formed.

In the case described in the section of (Preferable Design of Fragments of Nucleic Acid Strand), as shown in FIG. 1, appropriate alignment of fragments by hybridization, deprotection of "functional groups", and progress of a chemical reaction between a "functional group pair" (chemical ligation) simultaneously occur after the introducing step to form a functional nucleic acid molecule composed of 2 nucleic acid strands.

2. Nucleic Acid Combination (Outline of Nucleic Acid Combination)

A nucleic acid combination (nucleic acid combination for construction) to be used in a method for constructing a functional nucleic acid molecule according to the present invention includes all the "nucleic acid strands" for constituting a functional nucleic acid molecule, wherein at least one of the "nucleic acid strands" is contained as 2 or more "fragments" having a "functional group pair" at "corresponding ends", which mutually couples through a chemical reaction. In this regard, examples of a "nucleic acid combination" are the same as described in the section of (Introducing Step).

(Preferable Form of Nucleic Acid Combination)

In a preferable form of a nucleic acid combination, the "fragments" are designed such that the "functional nucleic acid molecule" has a hybridization region where hybridization occurs within the "nucleic acid strand" or hybridization occurs between different "nucleic acid strands", and that ligation between the "fragments" occurs in the hybridization region.

A more preferable form of a nucleic acid combination includes a first "nucleic acid strand" and a second "nucleic acid strand", which compose the "functional nucleic acid molecule" and can hybridize, wherein each of the 2 "nucleic acid strands" is contained as 2 "fragments" having a "functional group pair" at "corresponding ends", which mutually couples through a chemical reaction. Furthermore, the respective fragments are designed such that mutual ligation of "fragments" constituting a "first nucleic acid strand" and mutual ligation of "fragments" constituting a "second nucleic acid strand" occur at different places in the hybridization region (see also FIG. 1 and Example).

A further preferable form of a nucleic acid combination includes a "first RNA strand" and a "second RNA strand", which compose the "functional nucleic acid molecule" and can hybridize, wherein the "first RNA strand" is contained as a "first fragment" and a "second fragment" having a "functional group pair" at "corresponding ends", which mutually couples through a chemical reaction. Meanwhile, the "second RNA strand" is contained as a "third fragment" and a "fourth fragment" having a "functional group pair" at "corresponding ends", which mutually couples through a chemical reaction. Furthermore, the "first fragment" or the "second fragment" can hybridize with both the "third fragment" and the "fourth fragment", and the "third fragment" or the "fourth fragment" can hybridize with both the "first fragment" and the "second fragment" (see also the section of (Preferable Design of Fragments of Nucleic Acid Strand), FIG. 1 and Example).
(Application of Nucleic Acid Combination)

A nucleic acid combination according to the present invention may be packaged together with instructions for use describing the procedures for use (there is, however, no particular limitation on a recording medium, and those recorded in a paper medium or an electronic medium are acceptable). In the instructions for use, for example, the usage of a nucleic acid combination as described in the section of (Introducing Step) and the section of (Producing Step) is described. A nucleic acid combination may be a drug or a reagent kit according to an end use.

3. Others (Application of Construction Method of Functional Nucleic Acid Molecule)

A nucleic acid combination may be used for treating an individual of a non-human animal, such as a rodent like a mouse, a rat, and a guinea pig, a rabbit, a dog, and a cat, or a human individual. Namely, a nucleic acid combination may be administered to a non-human animal individual, or a human individual. Examples of an administration method are the same as the in vivo introduction methods listed above.

Furthermore, use of a nucleic acid combination on an individual of a non-human animal, such as a rodent like a mouse, a rat, and a guinea pig, a rabbit, a dog, and a cat, or a human individual is provided. A cell into which a nucleic acid combination has been introduced is provided. A cell into which a nucleic acid combination has been introduced retains the nucleic acid combination inside. A cell into which a nucleic acid combination has been introduced may be packaged together with instructions for use describing the procedures for use (there is, however, no particular limitation on a recording medium, and those recorded in a paper medium or an electronic medium are acceptable). In the instructions for use, for example, the usage of a cell as described in the section of (Producing Step) is described. A cell may be a drug or a reagent kit according to an end use.

4. Summary

As described above, the present invention includes the following.

1) A method for constructing a functional nucleic acid molecule comprising 1 or 2 nucleic acid strands, comprising an introducing step for introducing 2 or more fragments having at corresponding ends a functional group pair that can mutually couple through a chemical reaction into a cell, and a producing step for producing a functional nucleic acid molecule comprising 1 or 2 nucleic acid strands by ligating mutually the fragments through a reaction between the functional groups in the cell.

2) The method according to 1) above, wherein the functional nucleic acid molecule has a hybridization region where hybridization occurs within the nucleic acid strand(s) or between different nucleic acid strands, and the fragments are designed such that the mutual ligation of the fragments occurs in the hybridization region.

3) The method according to 2) above, wherein the functional nucleic acid molecule comprises the 2 nucleic acid strands of a first nucleic acid strand and a second nucleic acid strand and has the hybridization region where hybridization occurs between the different nucleic acid strands, each of the 2 nucleic acid strands is introduced in a cell as 2 fragments having at corresponding ends a functional group pair that can mutually couple through a chemical reaction, and the mutual ligation of fragments constituting the first nucleic acid strand and the mutual ligation of fragments constituting the second nucleic acid strand occur at different places in the hybridization region.

4) The method according to 3) above, wherein the functional nucleic acid molecule comprises a first RNA strand as the first nucleic acid strand and a second RNA strand as the second nucleic acid strand, the first RNA strand is introduced into a cell as a first fragment and a second fragment having at corresponding ends a functional group pair that can mutually couple through a chemical reaction, the second RNA strand is introduced into a cell as a third fragment and a fourth fragment having at corresponding ends a functional group pair that can mutually couple through a chemical reaction, and the first fragment or the second fragment can hybridize with both the third fragment and the fourth fragment, and the third fragment or the fourth fragment can hybridize with both the first fragment and the second fragment.

5) The method according to any one of 1) to 4) above, wherein the functional nucleic acid molecule has an RNA interference action in a cell.

6) The method according to any one of 1) to 5) above, wherein the functional group pair that can mutually couple through a chemical reaction is a combination of an electrophilic group and a nucleophilic group protected by a protecting group.

7) The method according to 6) above, wherein the nucleophilic group is a phosphorothioate group.

8) The method according to 6) or 7) above, wherein the electrophilic group is an iodoacetyl group, a bromoacetyl group, or an iodo group.

9) The method according to any one of 6) to 8) above, wherein the protecting group is eliminated by an endogenous substance in the cell, or light irradiation.

10) The method according to 6), 8), or 9) above, wherein when the nucleophilic group is a phosphorothioate group, the protecting group is any of the following (a) to (k).

[Formula 12]

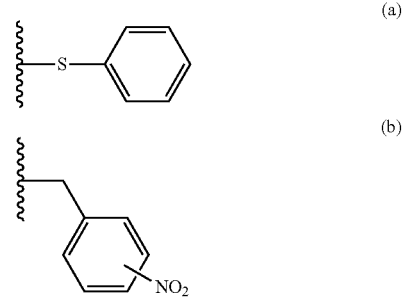

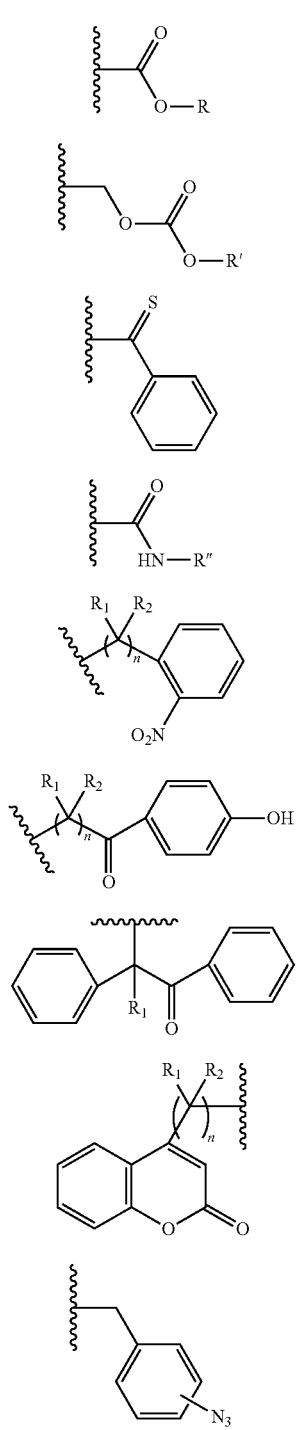

wherein R, R' and R" represent a substituted or unsubstituted alkyl group or aryl group; $R_1$ and $R_2$ independently represent a hydrogen atom or a C1 to C4 alkyl group; and n represents an integer from 1 to 3; in this regard, when n is 2 or 3, existing n number of $R_1$ may be different from each other, and existing n number of $R_2$ may be different from each other; and furthermore, a plurality of hydrogen atoms in a benzene ring in (a), (b), (e), (g), (h), (i), (j), and (k) may be independently replaced by a substituent.

11) A nucleic acid combination for constructing a functional nucleic acid molecule to be used in the method according to any one of 1) to 10) above, comprising the nucleic acid strands constituting a functional nucleic acid molecule, wherein at least one of the nucleic acid strands is contained as 2 or more fragments having at corresponding ends a functional group pair that can mutually couple through a chemical reaction.

12) The nucleic acid combination according to 11) above, wherein the functional nucleic acid molecule has a hybridization region where hybridization occurs within the nucleic acid strand(s) or between different nucleic acid strands, and the fragments are designed such that the mutual ligation of the fragments occurs in the hybridization region.

13) The nucleic acid combination according to 12) above, comprising the 2 nucleic acid strands of a first nucleic acid strand and a second nucleic acid strand, which can hybridize and constitute the functional nucleic acid molecule, wherein each of the 2 nucleic acid strands is contained as 2 fragments having at corresponding ends a functional group pair that can mutually couple through a chemical reaction, and the fragments are designed such that the mutual ligation of fragments constituting the first nucleic acid strand and the mutual ligation of fragments constituting the second nucleic acid strand occur at different places in the hybridization region.

14) The nucleic acid combination according to 13) above, comprising a first RNA strand as the first nucleic acid strand and a second RNA strand as the second nucleic acid strand to constitute the functional nucleic acid molecule, wherein the first RNA strand is contained as a first fragment and a second fragment having at corresponding ends a functional group pair that can mutually couple through a chemical reaction, the second RNA strand is contained as a third fragment and a fourth fragment having at corresponding ends a functional group pair that can mutually couple through a chemical reaction, and the first fragment or the second fragment can hybridize with both the third fragment and the fourth fragment, and the third fragment or the fourth fragment can hybridize with both the first fragment and the second fragment.

Embodiments of the present invention will be described in more detail by way of Example presented below. Needless to say, the present invention is not limited to the following Example, and there can be many modes in the details. Furthermore, the present invention is not limited to the aforedescribed embodiments, there can be many modifications within the scope of the claims, and embodiments to be obtained by an appropriate combination of technical means disclosed are included in the technical scope of the present invention. The contents of all the literatures described herein are hereby incorporated by reference.

EXAMPLE

1. Preparation of RNA

Design and Synthesis of RNA

Figure 2:
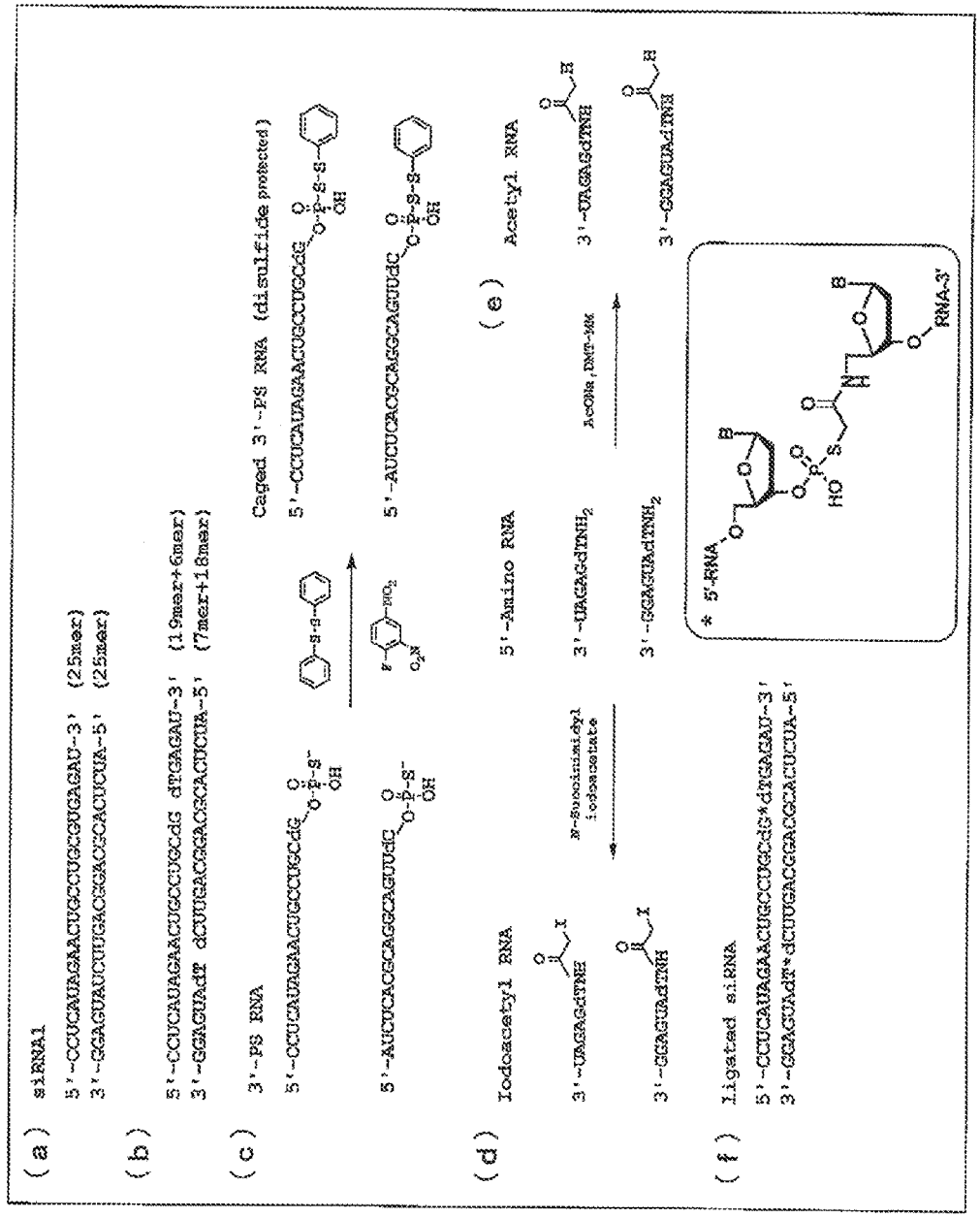
FIG. 2A-2F is a diagram showing sequences of various RNAs used in Example. A) siRNA. Upper 25 mer, SEQ ID NO:1; lower 25 mer, SEQ ID NO:2. B) siRNA. 19 mer, SEQ ID NO:3; 18 mer, SEQ ID NO:4. C) 3'-PS RNA and Caged 3'-PS RNA (disulfide). Upper left and right sequences, SEQ ID NO:3; lower left and right sequences, SEQ ID NO:4. D) Iodoacetyl RNA. E) Acetyl RNA. F) Ligated siRNA. Upper sequence, SEQ ID NO:5; lower sequence, SEQ ID NO:6.

Based on siRNA1 (FIG. 2 (a): SEQ ID NOs: 1 and 2) suppressing expression of a luciferase gene, RNAs were synthesized by dividing the sense strand and the antisense strand respectively to 3'-PS (phosphorothioate) RNAs and 5'-amino RNAs (FIG. 2 (b): SEQ ID NOs: 3 and 4).

All of the 3'-PS RNAs and 5'-amino RNAs were synthesized according to the phosphoramidite method by a DNA synthesizer (GeneWorld H8-SE). As an amidite reagent for RNA, a 2'-O-TOM protected form (Glen Research Corporation) was used, and for 3'-end phosphorylation, 3'-Phosphate CPG (Glen Research Corporation) and Sulfurizing Reagent (Glen Research Corporation) were used. For introduction of an amino dT to a 5'-end, 5'-Amino dT Phosphoramidite (Glen Research Corporation) was used. Deprotection of RNA was conducted according to a standard method, and 3'-PS RNAs and 5'-amino RNAs were used for the next reactions after only partial purification.

(Chemical Modification of Synthesized RNA)

By reacting 3'-PS RNAs of the synthesized sense strand and the antisense strand with diphenyl disulfide, caged 3'-PS RNAs were synthesized (FIG. 2 (c)). In this regard, with respect to the 3'-disulfide bond, elimination occurs after introduction into a cell by a biogenic thiol source such as GSH. For introduction of a disulfide bond to the 3'-PS RNA, a mixed liquid prepared with the composition according to Table 1 was incubated at room temperature for 6 hours.

TABLE 1

| 3'-PS RNA | 200 μM |
|---|---|
| Diphenyl disulfide (100 mM in DMSO) | 4 mM |
| 1-Fluoro-2,4-dinitrobenzene (20 mM in DMSO) | 2 mM |
| Tris-HCl (pH 7.2) | 50 mM |
| DMSO | up to 100 μL |

Furthermore, by reacting 5'-amino RNAs with respect to the sense strand and the antisense strand with N-succinimidyl iodoacetate, iodoacetylRNAs were synthesized (FIG. 2 (d)). For iodoacetylation of a 5'-amino RNA, a mixed liquid prepared with the composition according to Table 2 was incubated at room temperature for 2 hours.

TABLE 2

| 5'-amino RNA | 200 μM |
|---|---|
| N-Succinimidyl iodoacetate (80 mM in DMF) | 8 mM |
| Sodium borate buffer solution (pH 8.5) | 50 mM |
| H$_2$O | up to 100 μL |

(Preparation of RNA to be Used for Comparison)

Unmodified siRNAs (25 mer: sequences shown in FIG. 2 (a)) were synthesized by a DNA synthesizer (GeneWorld H8-SE) according to the phosphoramidite method similarly as syntheses of 3'-PS RNAs and 5'-amino RNAs, and full-length products were purified with a modified polyacrylamide gel.

Furthermore, 5'-amino RNAs with respect to the sense strand and the antisense strand were reacted with sodium acetate to synthesize acetyl RNAs having no reactivity with a 3'-PS RNA (FIG. 2 (e)). For acetylation of a 5'-amino RNA, a mixed liquid prepared with the composition according to Table 3 was incubated at room temperature for 2 hours.

TABLE 3

| 5'-amino RNA | 100 μM |
|---|---|
| Sodium acetate (100 mM in H$_2$O) | 5 mM |
| DMT-MM(100 mM in MeOH) | 5 mM |
| MeOH | up to 100 μL |

Furthermore, ligated siRNAs (FIG. 2 (f): SEQ ID NOs: 5 and 6) formed by ligation of a 3'-PS RNA and an iodoacetyl RNA were synthesized by ligating a 3'-PS RNA with an iodoacetyl RNA in vitro (cell-free system).

The thus synthesized caged 3'-PS RNAs, iodoacetyl RNAs, acetyl RNAs, and ligated siRNAs were analyzed and purified by HPLC (B conc. 0 to 40%, A solution: 50 mM TEAA, 5% acetonitrile in H$_2$O, B solution: 100% acetonitrile). Thereafter, the products were desalted using a Sep-Pak cartridge (eluted with 6 mL of 50% aqueous acetonitrile), and then concentrated using a centrifugal evaporator. The obtained RNAs were dissolved in ultrapure water, and diluted appropriately, and the solution concentrations were determined quantitatively by measuring the UV absorption spectrum.

2. Confirmation of Ligation In Vitro (Cell-Free System)

(Method)

For confirming occurrence of ligation in vitro between a caged 3'-PS RNA and an iodoacetyl RNA, a reaction was conducted with the composition according to Table 4. The lane 5 in Table 4 is a control without addition of GSH.

TABLE 4

| | lane | | |
|---|---|---|---|
| | 4 | 5 | Final Conc. |
| sense | | | |
| Iodoacetyl RNA (10 μM) | 1 | 1 | 0.5 μM |
| Caged 3'-PS RNA (10 μM) | 1 | 1 | 0.5 μM |
| antisense | | | |
| Iodoacetyl RNA (10 μM) | 1 | 1 | 0.5 μM |
| Caged 3'-PS RNA (10 μM) | 1 | 1 | 0.5 μM |
| GSH (1 mM) | 1 | — | 50 μM |
| 2x HBSS (+) | 10 | 10 | |
| Volume | up to 20 μL | | |

The composition of HBSS is 1.8 mM of CaCl$_2$, 0.49 mM of MgCl$_2$, and 0.41 mM of MgSO$_4$, and the pH is 7.4.

The mixed liquid was incubated at 37° C. for 30 min, and then a loading buffer (100% formamide, 0.5% XC) was added, followed by incubation at 90° C. for 5 min. The reaction solution was electrophoresed in a 20% modified acrylamide gel and analyzed by staining with CYBR Green II for 30 min. As markers, a 25 mer RNA strand was loaded in lane 1, a 19 mer caged 3'-PS RNA (sense strand) in lane 2, and a 18 mer caged 3'-PS RNA (antisense strand) in lane 3 similarly.

(Result)

Figure 3:
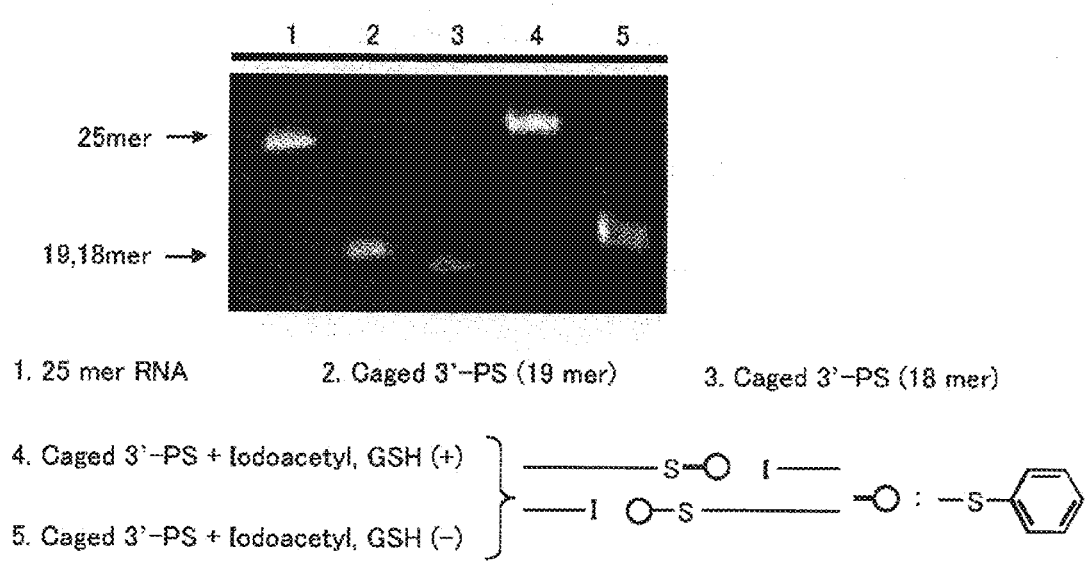
FIG. 3 is a diagram showing the results of in vitro ligation in Example.

The result of the electrophoresis is shown in FIG. 3. It could be confirmed that ligation of the 3'-PS RNA and the iodoacetyl RNA progressed to form a 25 mer RNA strand (lane 4).

Furthermore, even when 2 μL of GSH was added to 4 μL of a caged 3'-PS RNA and 4 μL of an iodoacetyl RNA of only the sense strand to carry out similarly a ligation reaction, a 25 mer single strand RNA was also produced.

3. Measurement of RNA Interference Effect Using Mammalian Culture Cell System-1

(Method)

HeLa-Luc cells (purchased from Caliper (A PerkinElmer Company)) were cultured in a DMEM culture medium (made by Wako Pure Chemical Industries, Ltd.) containing 10% FBS at 37° C. in 5% CO$_2$, and dispensed to a 96-well plate 100 μL per each well to be 4.0×10$^3$ cells/well. After additional culture at 37° C. in 5% CO$_2$ for 24 hours and at an approx. 60% confluent condition, various RNAs (3'-PS RNAs and iodoacetyl RNAs of the sense strand and the antisense strand) were cotransfected using a transfection reagent Gene Silencer (made by Genlantis) according to the protocol attached to the transfection reagent. The concentrations of the RNAs were set at 25, 50, or 100 nm.

Specifically, in a state that 50 μL of HBSS (+) was added to cells, the following mix solution for transfection was added. The composition of the mix solution for transfection is as in Table 5.

TABLE 5

| Gene Si lencer | 1 μL |
|---|---|
| 2XHBSS (+) | 12.5 μL |
| Diluted liquid of siRNA | 2.5 μL |
| 2XHBSS (+) | 7.5 μL |
| RNA (1.25 μM) | 2, 4 or 8 μL |
| DDW | up to 100 μL |

After the transfection followed by incubation at 37° C. in 5% $CO_2$ for 6 hours, the medium was changed to a DMEM culture medium containing 10% FBS. After another incubation at 37° C. for 18 hours, a luciferase expression amount was determined quantitatively using a Luciferase Assay System (made by Promega Corporation) according to the attached protocol (conditions: reagent amount 50 μL, delay time 2 sec, reading time 10 sec; equipment: Muthras LB 940 (made by Berthold Technologies GmbH & Co. KG)).

For comparison, a scramble siRNA (25 nm), an unmodified siRNA (25 nm), a ligated siRNA (25 nm), a caged 3'-PS RNA+an acetyl RNA (25 nm, 50 nm or 100 nm), only a caged 3'-PS RNA (100 nm), only an iodoacetyl RNA (100 nm), and only an acetylRNA (100 nm) were transfected as above, and luciferase expression amounts were determined quantitatively.
(Results)

Figure 4:
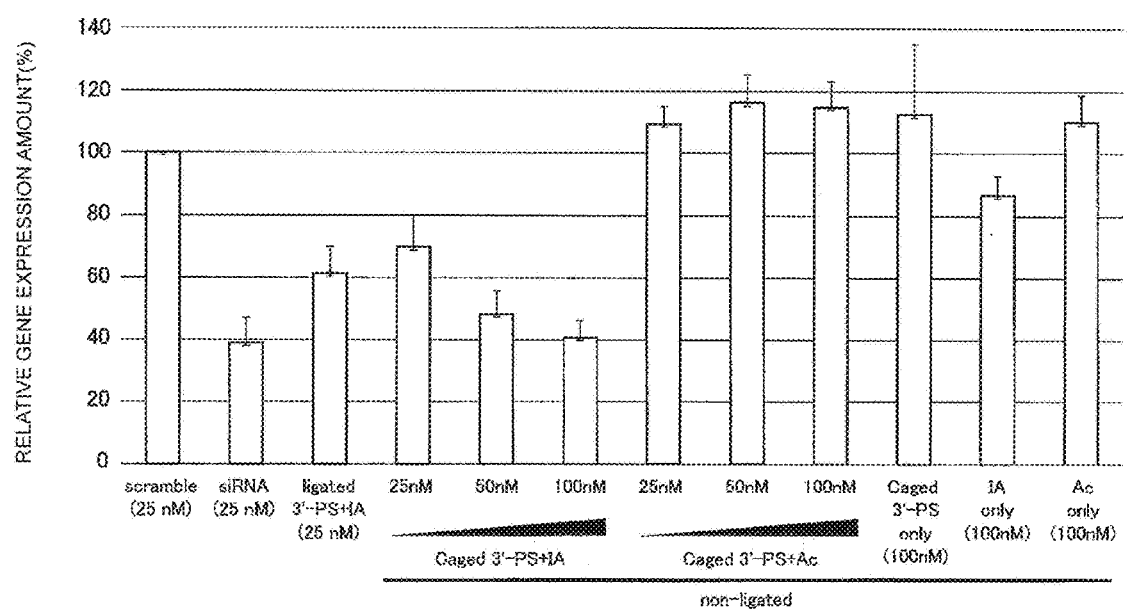
FIG. 4 is a diagram showing the results of expression of a luciferase gene in Example.

The results of luciferase gene expression are shown in FIG. 4. When a caged 3'-PS RNA and an iodoacetyl RNA (IA), which were not ligated together, were introduced into a cell, the expression of a luciferase gene was low and sufficient inhibitory activity was observed. On the other hand, when a caged 3'-PS RNA and an acetyl RNA (Ac), which were not ligated together, were introduced, the inhibitory activity was not observed. This result suggests that a 3'-PS RNA and an iodoacetyl RNA formed a ligated siRNA in a cell through a ligation reaction, and the same suppressed gene expression.

From this, it has become clear that a functional RNA can be constructed in a cell by importing the functional RNA in fragments into a cell.

4. Measurement of RNA Interference Effect Using Mammalian Culture Cell System-2 (Transfection by Osmotic Shock (Method)

HeLa-Luc cells were cultured in a DMEM culture medium (made by Wako Pure Chemical Industries, Ltd.) containing 10% FBS at 37° C. in 5% $CO_2$, recovered at an approx. 60% confluent condition, and washed with PBS. Next, the cells were suspended in a mixed liquid (10 μL) of a hypertonic buffer and various RNAs (3'-PS RNAs and iodoacetyl RNAs for a sense strand and an antisense strand), and incubated at 37° C. for 10 min. Sterilized water (52.9° L) was added thereto, and the mixture was further incubated 37° C. for 10 min. Thereafter, the cells were recovered and washed with PBS. Next, the recovered cells were suspended in a DMEM (400 μL) containing 10% FBS, and dispensed to a 96-well plate 100 μL per each well. The composition of the hypertonic buffer is 2.1 M of sucrose, 7.5% PEG (2000), and 150 mM of HEPES (pH 7.3) in an HBSS buffer. The composition of the mixed liquid (10 μL) of a hypertonic buffer and various RNAs is as shown in Table 6.

TABLE 6

| 1.5 × hypertonic buffer | 6.7 μL |
|---|---|
| RNA (30 μM) | 0.33 μL |
| DDW | up to 10 μL |

After the transfection, the cells were incubated at 37° C. in 5% $CO_2$ for 24 hours, and a luciferase expression amount was determined quantitatively using a Luciferase Assay System (made by Promega Corporation) according to the attached protocol (conditions: reagent amount 30 μL, delay time 2 sec, reading time 10 sec; equipment: Muthras LB 940 (made by Berthold Technologies GmbH & Co. KG)). Furthermore, using a BCA protein assay kit (made by Thermo Scientific), a protein amount was determined quantitatively according to the attached protocol to correct the luciferase expression amount.

For comparison, a scramble siRNA, and an unmodified siRNA were transfected similarly as above, and the luciferase expression amounts were determined quantitatively and corrected.
(Results)

Figure 5:
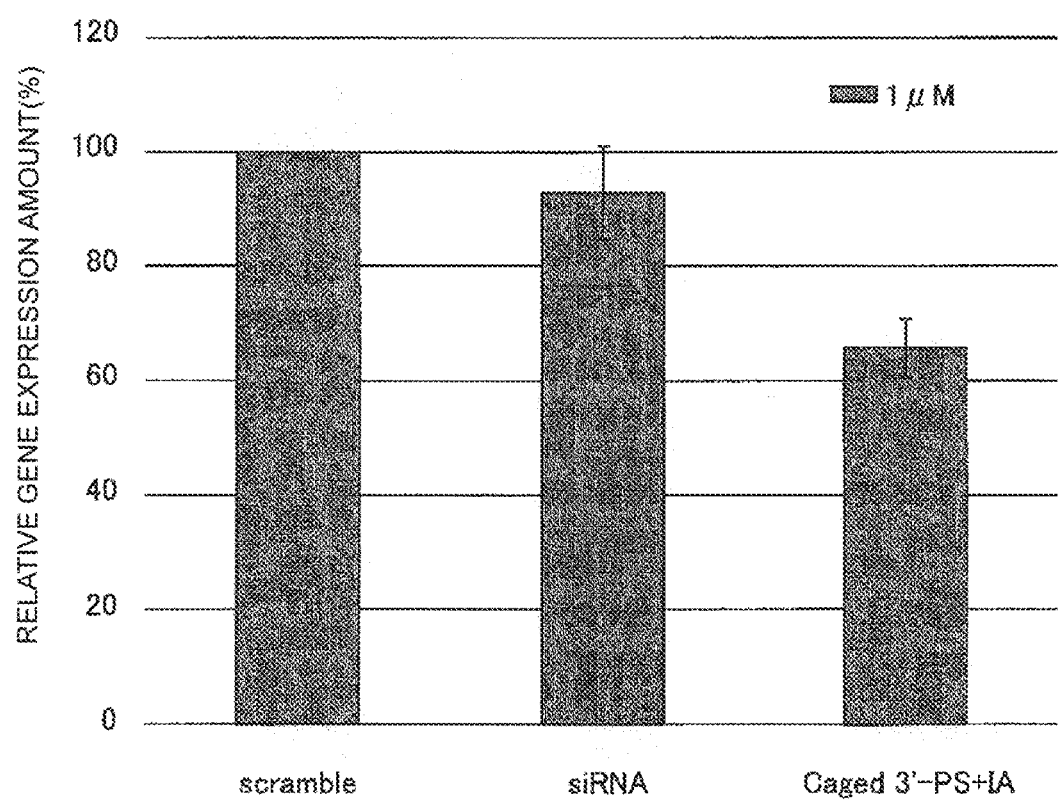
FIG. 5 is a diagram showing the results of expression of a luciferase gene in Example.

The results of luciferase gene expression are shown in FIG. 5. When a caged 3'-PS RNA and an iodoacetyl RNA (IA), which were not ligated togethet, were introduced in a cell, the expression of a luciferase gene was low and highly inhibited in comparison to a case where an unmodified siRNA was introduced into a cell. This result suggests that the cell membrane permeability was improved by introducing an siRNA after fragmentation to a caged 3'-PS RNA and an IA.

It has become clear that, by introducing a functional RNA in fragments into a cell, the cell membrane permeability is improved and a larger amount of a functional RNA can be introduced efficiently into a cell.

5. Measurement of Immune Response Using Mammalian Culture Cell (Method)

T98G cells (obtained from Riken BioResource Center) were cultured in an RPMI-1640 culture medium (made by Wako Pure Chemical Industries, Ltd.) containing 10% FBS at 37° C. in 5% $CO_2$, and dispensed to a 24-well plate 300 μL per each well to be $4.0 \times 10^4$ cells/well. After additional culture at 37° C. in 5% $CO_2$ for 24 hours and at approx. 70% confluent condition, various RNAs (3'-PS RNAs and iodoacetyl RNAs of the sense strand and the antisense strand) were cotransfected using a transfection reagent Lipofectamine 2000 (Invitrogen) according to the protocol attached to the transfection reagent. For comparison, transfection was conducted similarly for the cases of no RNA, poly I:C and an unmodified siRNA. The concentration of the RNA was 100 nm (final volume 300 μL). The composition of the mixed solution for transfection was as shown in Table 7.

TABLE 7

| Lipofect amine 2000 | 1.0 μL |
|---|---|
| HBSS (+) buffer | 293 μL |
| RNA (5 μM) or DDW | 6.0 μL |
| total | 300 μL |

After the transfection, the cells were incubated at 37° C. in 5% $CO_2$ for 6 hours, and 300 μL of an RPMI-1640 culture medium containing 20% Serum was added to each well. After incubation at 37° C. for another 18 hours, total RNA was recovered using ISOGEN (made by Nippon Gene Co., Ltd.) according to the attached protocol. The expression amounts of IFN-β and β-Actin were measured using the recovered RNA and One Step PrimeScript(R) RT-PCR Kit (Perfect Real Time) (made by Takara Bio Inc.). From the obtained results, a relative IFN-β expression amount was calculated by correcting an IFN-β expression amount with a β-Actin expression amount using a ΔΔCt method. The composition of a reaction solution used for the real time PCR is as shown in Table 8. Meanwhile, the reaction conditions for the real time PCR are as shown in Table 9.

TABLE 8

| | |
|---|---|
| 2 × One Step SYBR RT-PCR Buffer 4 | 5.0 μL |
| primer mix (10 μm) | 0.3 μL |
| TaKaRa Ex Taq HS Mix | 0.6 μL |
| Primer Script PLUS RTase Mix | 0.2 μL |
| total RNA (10 ng/μL) | 1.0 μL |
| RNase free water | 2.9 μL |
| total | 10 μL |

TABLE 9

CFX86 Touch ™ Real-Time PCR Detection System (Bio-Rad)

| Temperature | time | |
|---|---|---|
| 42° C. | 5 min | |
| 42° C. | 10 sec | |
| 95° C. | 5 sec | 40 cycles |
| 60° C. | 30 sec | |

(Results)

Figure 6:
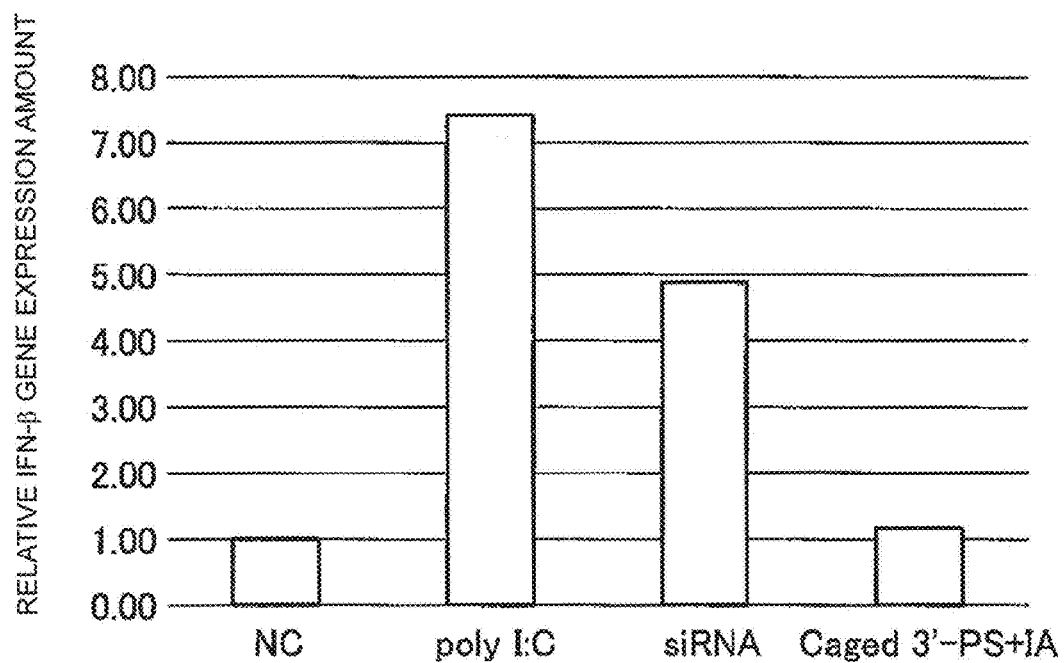
FIG. 6 is a diagram showing the measurement results of immune response in Example.

The results are shown in FIG. 6. It was confirmed that, when an siRNA or a poly I:C was introduced into a cell, the expression amount of IFN-β increased, compared to a negative control (NC), which was not transfected with an RNA. On the other hand, when a caged 3'-PS RNA and an iodoacetyl RNA (IA), which were not ligated together, were introduced into a cell, a change in the expression amount of IFN-β was not observed. This result indicates that an immune response which is induced by a not-fragmented siRNA can be avoided by introduction of an siRNA in fragments into a cell.

It has become clear as above that an immune response which is induced by a not-fragmented functional RNA can be avoided by introduction of a functional RNA in fragments into a cell.

INDUSTRIAL APPLICABILITY

The present invention can be applied to a field of a drug, a reagent, etc. utilizing a functional nucleic acid molecule.

The invention claimed is:

1. An intracellular buildup method of a functional nucleic acid molecule, comprising:
a step of introducing into a cell two or more fragments having corresponding ends modified with functional groups to be ligated by an intracellular chemical reaction, and
a step of ligating the fragments by reacting the functional groups in the cell to generate said functional nucleic acid molecule.

2. The method according to claim 1, wherein the functional nucleic acid molecule has a hybridization region where hybridization occurs within nucleic acid strand(s) or between different nucleic acid strands, and the ligation of the fragments occurs in the hybridization region.

3. The method according to claim 2, wherein the functional nucleic acid molecule comprises two nucleic acid strands of a first nucleic acid strand and a second nucleic acid strand and has a hybridization region where hybridization occurs between said two nucleic acid strands,
each of the two nucleic acid strands is introduced into the cell as two fragments having the corresponding ends modified with the functional groups to be ligated by the intracellular chemical reaction, and
the ligation of fragments constituting the first nucleic acid strand and the ligation of fragments constituting the second nucleic acid strand occur at different places in the hybridization region.

4. The method according to claim 3, wherein the functional groups that can be ligated by the intracellular chemical reaction are a combination of an electrophilic group and a nucleophilic group protected by a protecting group.

5. The method according to claim 4, wherein the nucleophilic group is a phosphorothioate group.

6. The method according to claim 5, wherein the protecting group is any of the following (a) to (k),

[Formula 1]

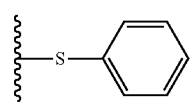

(a)

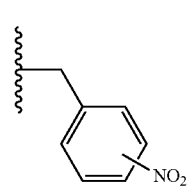

(b)

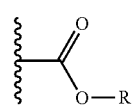

(c)

-continued

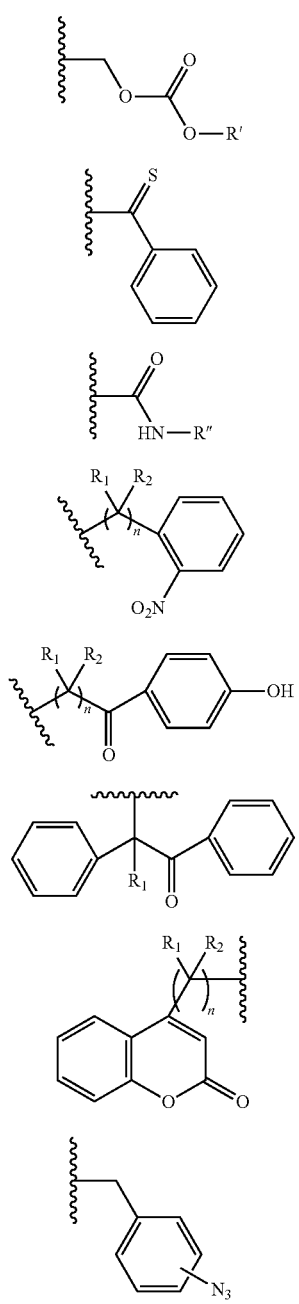

wherein R, R' and R" represent a substituted or unsubstituted alkyl group or aryl group; R1 and R2 independently represent a hydrogen atom or a C1 to C4 alkyl group; and n represents an integer from 1 to 3; when n is 2 or 3, existing n number of R1 may be different from each other, and existing n number of R2 may be different from each other; and furthermore, a plurality of hydrogen atoms in a benzene ring in (a), (b), (e), (g), (h), (i), (j), and (k) may be independently replaced by a substituent.

7. The method according to claim 4, wherein the electrophilic group is an iodoacetyl group, a bromoacetyl group, or an iodo group.

8. The method according to claim 4, wherein the protecting group is eliminated by an endogenous substance in the cell or light irradiation.

9. An intracellular buildup method of an active siRNA, comprising:
a step of introducing into a cell at least one of a first RNA strand and a second RNA strand, which constitute said siRNA, as two or more fragments having corresponding ends modified with functional groups to be ligated by an intracellular chemical reaction, and
a step of ligating the fragments by reacting the functional groups in the cell to generate said siRNA,
wherein the length of the fragments is less than 20 mer and the length of the siRNA is more than 20 mer.

10. The method according to claim 9, wherein the siRNA has a hybridization region where hybridization occurs between the first RNA strand and the second RNA strand, and the ligation of the fragments occurs in the hybridization region.

11. The method according to claim 10, wherein each of the first RNA strand and the second RNA strand is introduced into the cell as two fragments having the corresponding ends modified with the functional groups to be ligated by the intracellular chemical reaction, and the ligation of fragments constituting the first RNA strand and the ligation of fragments constituting the second RNA strand occur at different places in the hybridization region.

12. The method according to claim 11, wherein the functional groups that can be ligated by the intracellular chemical reaction are a combination of an electrophilic group and a nucleophilic group protected by a protecting group.

13. The method according to claim 12, wherein the nucleophilic group is a phosphorothioate group.

14. The method according to claim 13, wherein the protecting group is any of the following (a) to (k),

[Formula 1]

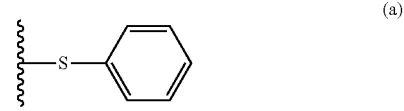 (a)

 (b)

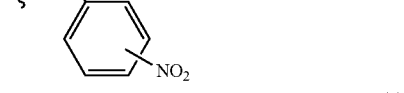 (c)

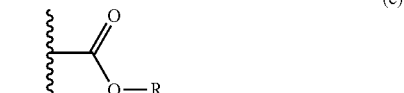 (d)

 (e)

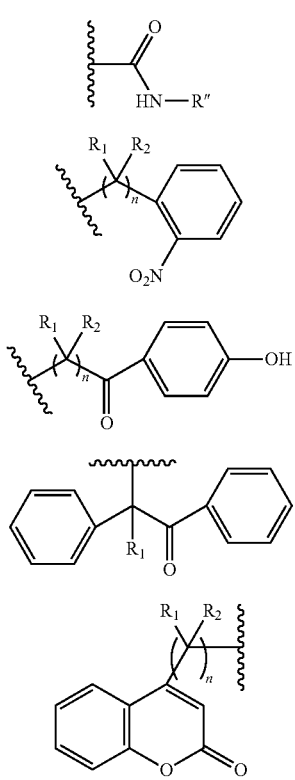

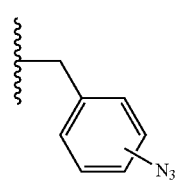

wherein R, R' and R" represent a substituted or unsubstituted alkyl group or aryl group; R1 and R2 independently represent a hydrogen atom or a C1 to C4 alkyl group; and n represents an integer from 1 to 3; when n is 2 or 3, existing n number of R1 may be different from each other, and existing n number of R2 may be different from each other; and furthermore, a plurality of hydrogen atoms in a benzene ring in (a), (b), (e), (g), (h), (i), (j), and (k) may be independently replaced by a substituent.

15. The method according to claim 12, wherein the electrophilic group is an iodoacetyl group, a bromoacetyl group, or an iodo group.

16. The method according to claim 12, wherein the protecting group is eliminated by an endogenous substance in the cell or light irradiation.

* * * * *

UNITED STATES PATENT AND TRADEMARK OFFICE
CERTIFICATE OF CORRECTION

PATENT NO. : 9,598,713 B2
APPLICATION NO. : 14/381681
DATED : March 21, 2017
INVENTOR(S) : Hiroshi Abe, Yoshihiro Ito and Hideto Maruyama It is certified that error appears in the above-identified patent and that said Letters Patent is hereby corrected as shown below:

On the Title Page

In (73) Assignee, "Japanese Science and Technology Agency" should read --JAPAN SCIENCE AND TECHNOLOGY AGENCY--.

Signed and Sealed this
Second Day of May, 2017

Michelle K. Lee
*Director of the United States Patent and Trademark Office*